United States Patent [19]

Srebnik et al.

[11] Patent Number: 4,754,891
[45] Date of Patent: Jul. 5, 1988

[54] BOTTLE FOR AN ENTERAL NUTRITION DELIVERY SYSTEM

[75] Inventors: Jack Srebnik, Guilford; Robert Reese, Seymour, both of Conn.

[73] Assignee: Sherwood Medical Company, St. Louis, Mo.

[21] Appl. No.: 53,060

[22] Filed: May 22, 1987

Related U.S. Application Data

[62] Division of Ser. No. 831,362, Feb. 20, 1986, Pat. No. 4,688,595.

[51] Int. Cl.$^4$ .............................................. B65D 1/02
[52] U.S. Cl. .................................... 215/309; 215/1 C
[58] Field of Search ................. 215/1 C, 1 A, 100 R, 215/307, 309; 222/211, 215

[56] References Cited

U.S. PATENT DOCUMENTS

| | | | |
|---|---|---|---|
| 2,755,972 | 7/1956 | Nave et al. | 222/211 |
| 3,921,630 | 11/1975 | McPhee | 215/1 C X |
| 3,964,629 | 6/1976 | McCabe | 215/100 R X |
| 4,159,790 | 7/1979 | Bailey | 222/211 |
| 4,301,933 | 11/1981 | Yoshino | 215/1 C |
| 4,340,157 | 7/1982 | Darner | 222/211 |

Primary Examiner—Donald F. Norton
Attorney, Agent, or Firm—Brumbaugh, Graves, Donohue & Raymond

[57] ABSTRACT

A bottle for an enteral delivery system is provided with vertical sidewalls which taper inwardly near the base portion. The tapered portions of the sidewalls have outwardly extending tabs for engaging recesses on a corresponding base support. The tabs do not extend outwardly further than the vertical sidewalls.

4 Claims, 2 Drawing Sheets

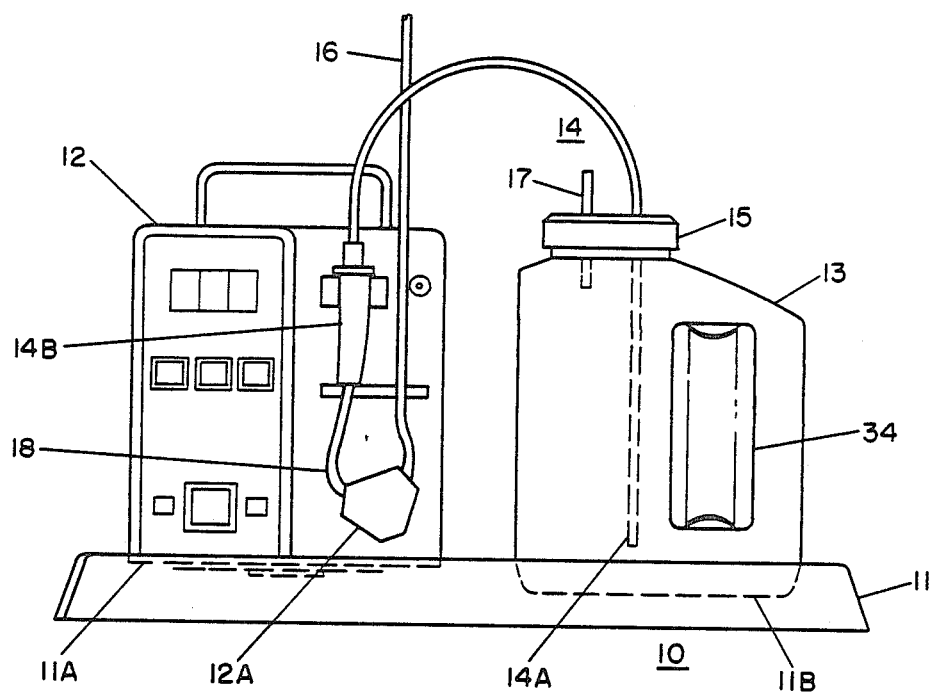
FIG. 1
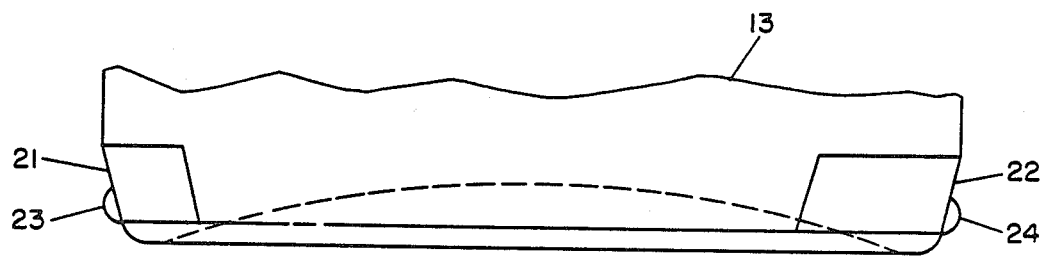
FIG. 2
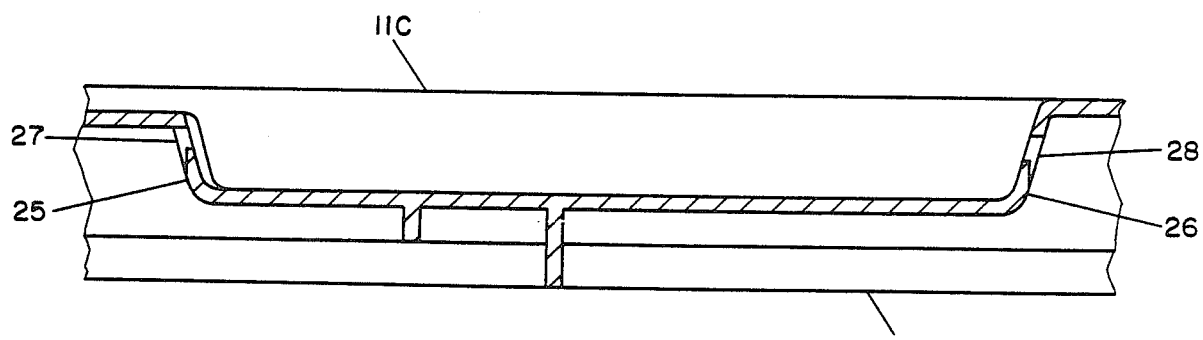

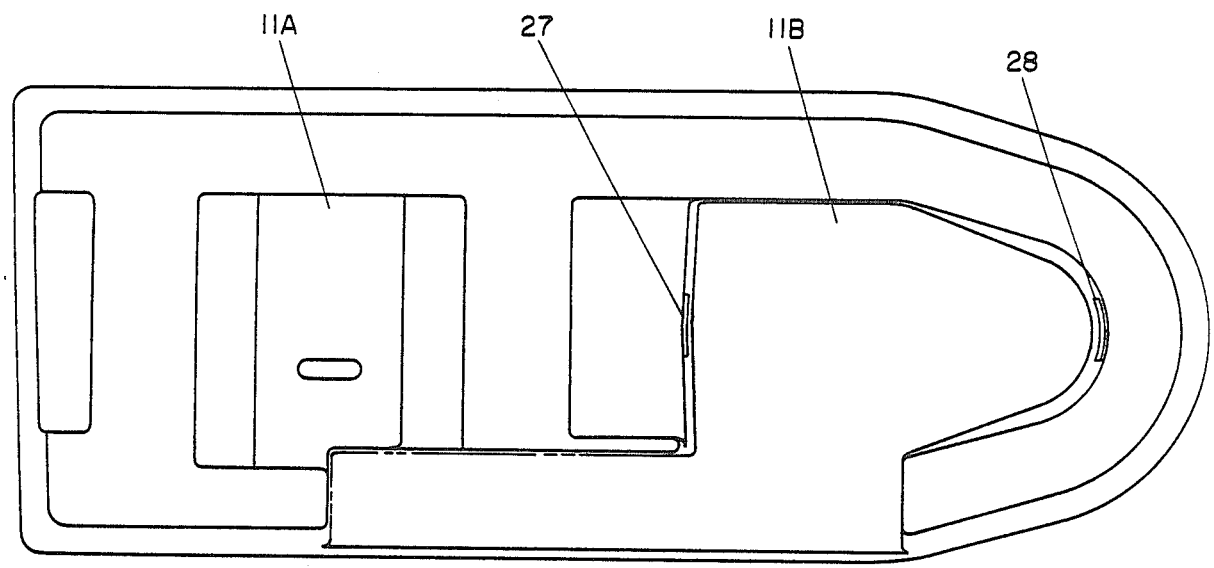
FIG. 4
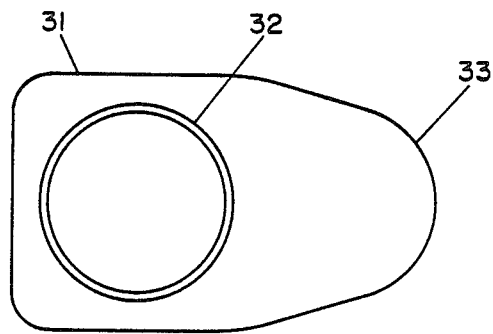
FIG. 5
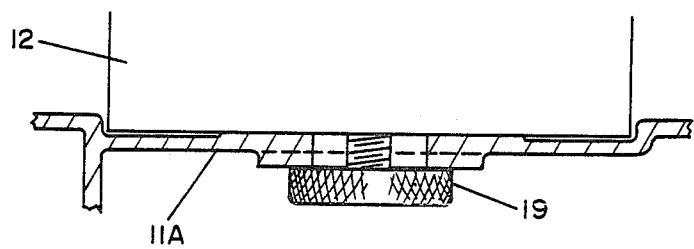

BOTTLE FOR AN ENTERAL NUTRITION DELIVERY SYSTEM

This application is a division of application Ser. No. 831,362, filed on Feb. 20, 1986, now U.S. Pat. No. 4,688,595.

This invention relates to an enteral nutrition delivery system.

BACKGROUND OF THE INVENTION

Enteral nutrition delivery systems generally include a bottle which contains the enteral fluid which is to be fed to the digestive tract of a patient, an infusion pump to regulate the rate of flow of the fluid from the bottle to the patient, and tubing interconnecting the bottle, pump, and patient. Typically, the bottle is mounted on a pole in an inverted position and the pump is separately mounted to the pole. If the patient wishes to move about, the pole must be rolled or carried along with the patient. This is inconvenient.

SUMMARY OF THE INVENTION

The present invention provides an integrated delivery system that makes it possible for the patient to move about without the inconvenience of having to move a mounting pole.

In particular, in an embodiment of the invention, the pump and the bottle are supported on a common base, the base including a first platform portion to which the pump may be firmly secured and a second platform portion recessed to receive the bottle, the bottle having tabs which fit into openings in the recessed portion for convenient secure locking. Tubing interconnects the bottle and pump and also includes a section for supplying the nutrient to the patient. By carrying the base, there is carried the pump, bottle, and tubing.

BRIEF DESCRIPTION OF THE DRAWING

FIG. 1 shows the assembly of base, pump, bottle and tubing in accordance with the invention;

FIG. 2 shows on an expanded scale the details of the bottom of the bottle included in the assembly;

FIG. 3 shows on an expanded scale the detail of the recess in the base;

FIG. 4 is a top view of the base;

FIG. 5 is a top view of the bottle; and

FIG. 6 illustrates how the pump is secured to the base.

DESCRIPTION OF EXEMPLARY EMBODIMENT

With reference now to the drawing, the assembly 10 seen in FIG. 1 includes the base 11 which includes platform region 11A which supports the infusion pump 12 and platform region 11B which supports the bottle 13 containing the enteral fluid to be fed to the patient. A tubing set includes the section 14 which extends, through a cap 15 closing the bottle opening, along section 14A to the bottom of bottle 13 and connects at its opposite end to a drip chamber 14B. A flexible tube section 18 engages the pump rotor 12A and connects to output section 16 which connects to the patient feeding tube. A short tube section 17 is used to vent the bottle. Section 17 includes a valve to permit flow of air into the bottle but prevent flow of air or fluid out.

The infusion pump 12 is secured to the first platform 11A of the base in the manner shown in FIG. 6. A screw 19 threads through the platform into a fitting (not shown) in the bottom of the pump housing. Tightening the screw secures the pump to the base.

The bottle advantageously is designed to facilitate both securing to and removal from the base. To this end, as seen in FIG. 2, the bottom of the bottle 13 is provided with an opposed pair of sidewall portions 21, 22 which are tapered inwardly and each of these tapered portions is provided with an outwardly extending locking tab 23, 24. To complement this bottle, as seen in FIG. 3, the platform region 11B of the base includes a recess 11C which has a pair of sidewalls 25, 26 which are tapered outwardly and each of which is provided with an opening 27, 28 for receiving one of the tabs in the bottle. The tapers of the sidewalls of the bottle and of the base recess are matched to ensure a good fit of the bottle in the recess. The tabs and the openings are appropriately designed to facilitate easy insertion and withdrawal consistent with secure holding. Preferably tabs 23, 24 do not extend beyond the vertical portions of the sidewalls to permit easy packing of bottles in close proximity. It is found advantageous to have one recess sidewall slightly higher than the other as seen in FIG. 3 to facilitate fitting the tabs in the openings.

FIG. 5 is a top view showing the profile of a preferred form of bottle. In particular, as seen from FIG. 1 and FIG. 5, the bottle includes a main section 31 which is essentially rectangular in cross section (FIG. 5) and includes the circular opening 32 and a gripping section 33 which is semi-elliptical in cross section (FIG. 5) and is provided with a pair of oppositely located indented regions 34 (FIG. 1) to facilitate gripping during insertion in and removal from the base.

FIG. 4 shows a top view of a typical base and includes the first platform region 11A where the pump is secured and the second platform region 11B which is recessed to accept the bottle.

Advantageously, the bottle and the base are of polystyrene for ease of manufacture and of cleaning consistent with good strength. Of course, other materials can be used. The bottle advantageously is of a wall thickness to be relatively flexible. The use of flexible material for the bottle facilitates priming of the drive chamber 14B and pump tube 18 by squeezing the bottle. Since vent tube 17 includes a valve, fluid is thus forced through the tube to the drip chamber and pump tube by manually squeezing the bottle. The base advantageously is an integral molded member of sufficient thickness to be relatively rigid.

It is to be understood that variations may be made in the specific components described without departing from the spirit and scope of the invention.

We claim:

1. A bottle for an enteral nutrition apparatus having a base support, comprising a flexible plastic bottle and a cap, said plastic bottle having a base portion and vertical sidewalls, said vertical sidewalls having lower portions tapered toward each other near said base portion and including integrally formed tabs extending outwardly on opposite sides of said tapered lower portions, said tabs having outer tab surface portions which face upwardly with respect to said vertical sidewalls to thereby securely hold said bottle against vertical movement when said bottle is inserted into said base support and said tabs extending a distance from said tapered lower portions which does not extend beyond said vertical sidewalls, and said cap including a vent opening arranged between the interior of said cap and the exterior of said cap having a valve to permit flow of air into said bottle, but prevent flow of air or fluid from said bottle, and said cap including a fluid tube extending therethrough and having a fluid inlet opening near the bottom of said bottle.

2. A bottle for an enteral nutrition apparatus including a base support, comprising a flexible plastic bottle and a cap, said plastic bottle having a base portion and vertical sidewalls, said vertical sidewalls having lower portions tapered toward each other near said base portion and including integrally formed tabs extending outwardly on opposite sides of said tapered lower portions, said tabs having outer tab surface portions which face upwardly with respect to said vertical sidewalls to thereby securely hold said bottle against vertical movement when said bottle is inserted into said base support and said tabs extending a distance from said tapered lower portions which does not extend beyond said vertical sidewalls.

3. A bottle for an enteral nutrition apparatus including a base support, comprising a flexible plastic bottle and a cap, said plastic bottle having a base portion and vertical sidewalls, said vertical sidewalls extending to said base portion proximate a horizontal bottom of said base portion, said base portion having a tapered portion tapering inwardly from said vertical sidewalls to said bottom and including integrally formed tabs extending outwardly on opposite sides of said tapered portion, said tabs having outer tab surface portions which face upwardly with respect to said vertical sidewalls to thereby securely hold said bottle against vertical movement when said bottle is inserted into said base support and said tabs extending a distance from said tapered portions which does not extend beyond said vertical sidewalls.

4. A bottle for an enteral nutrition apparatus including a base support, comprising a flexible plastic bottle and a cap, said plastic bottle having a base portion and vertical sidewalls, said vertical sidewalls extending to said base portion proximate a horizontal bottom of said base portion, said base portion having a tapered portion tapering inwardly from said vertical sidewalls to said bottom and including integrally formed tabs extending outwardly on opposite sides of said tapered portion, said tabs having outer tab surface portions which face upwardly with respect to said vertical sidewalls to thereby securely hold said bottle against vertical movement when said bottle is inserted into said base support and said tabs extending a distance from said tapered portions which does not extend beyond said vertical sidewalls, wherein said bottom has a width and a length greater than said width, and wherein said tabs extend in opposite lengthwise directions from said base portion.

* * * * *